United States Patent
Rizzardini et al.

(10) Patent No.: US 12,204,694 B2
(45) Date of Patent: Jan. 21, 2025

(54) METHOD FOR DETECTING A WRIST-TILT GESTURE AND AN ELECTRONIC UNIT AND A WEARABLE ELECTRONIC DEVICE WHICH IMPLEMENT THE SAME

(71) Applicant: STMICROELECTRONICS S.r.l., Agrate Brianza (IT)

(72) Inventors: Federico Rizzardini, Settimo Milanese (IT); Lorenzo Bracco, Chivasso (IT); Stefano Paolo Rivolta, Desio (IT)

(73) Assignee: STMICROELECTRONICS S.r.l., Agrate Brianza (IT)

( * ) Notice: Subject to any disclaimer, the term of this patent is extended or adjusted under 35 U.S.C. 154(b) by 4 days.

(21) Appl. No.: 17/862,937

(22) Filed: Jul. 12, 2022

(65) Prior Publication Data

US 2022/0342486 A1 Oct. 27, 2022

Related U.S. Application Data

(63) Continuation of application No. 17/067,519, filed on Oct. 9, 2020, now Pat. No. 11,422,634.

(30) Foreign Application Priority Data

Oct. 16, 2019 (IT) .................. 102019000019037

(51) Int. Cl.
  *G06F 3/01* (2006.01)
  *G01P 15/14* (2013.01)
  *G06F 1/16* (2006.01)
(52) U.S. Cl.
  CPC .............. *G06F 3/017* (2013.01); *G01P 15/14* (2013.01); *G06F 1/163* (2013.01)

(58) Field of Classification Search
  None
  See application file for complete search history.

(56) References Cited

U.S. PATENT DOCUMENTS

| | | | |
|---|---|---|---|
| 8,342,045 B2 | 1/2013 | Maxwell et al. | |
| 8,463,576 B2 | 6/2013 | Yuen et al. | |
| 8,786,547 B2 * | 7/2014 | Soldan | G06F 3/0346 345/157 |
| 8,996,332 B2 | 3/2015 | Kahn et al. | |

(Continued)

FOREIGN PATENT DOCUMENTS

WO WO 2016022496 A2 2/2016

*Primary Examiner* — Tuyetlien T Tran
(74) *Attorney, Agent, or Firm* — Seed IP Law Group LLP

(57) ABSTRACT

An electronic device has an input which, in operation, receives an input stream of accelerometer data samples indicative of acceleration values along at least one axis. The devices includes circuitry, coupled to the input. The circuitry, in operation, executes an automatic-learning algorithm on blocks of samples of the input stream of accelerometer data samples to identify, for each block, a corresponding condition-of-user-movement from among a plurality of determined conditions-of-user-movement. The circuitry generates a plurality of streams of samples based on the input stream of accelerometer data samples, and for each condition of movement identified, selects a corresponding stream of samples of the plurality of streams of samples. The circuitry executes a wrist-tilt gesture detection algorithm using samples of the selected stream of the plurality of streams of samples.

27 Claims, 8 Drawing Sheets

(56) References Cited

U.S. PATENT DOCUMENTS

| | | | |
|---|---|---|---|
| 9,582,080 B1* | 2/2017 | Tilton | G06F 3/015 |
| 10,275,200 B2 | 4/2019 | Kang et al. | |
| 10,505,875 B1* | 12/2019 | Jenks | H04L 51/10 |
| 10,540,083 B2* | 1/2020 | Goel | G06N 7/01 |
| 10,824,954 B1 | 11/2020 | Tilton et al. | |
| 10,973,440 B1* | 4/2021 | Martin | G06T 13/40 |
| 11,045,116 B1* | 6/2021 | Martin | A61B 5/112 |
| 2004/0227742 A1 | 11/2004 | Fateh et al. | |
| 2009/0265671 A1* | 10/2009 | Sachs | G06F 3/0346 715/863 |
| 2010/0245131 A1 | 9/2010 | Graumann | |
| 2011/0312279 A1* | 12/2011 | Tsai | H04W 4/21 455/67.11 |
| 2012/0306745 A1 | 12/2012 | Moore et al. | |
| 2013/0158686 A1 | 6/2013 | Zhang et al. | |
| 2014/0257533 A1 | 9/2014 | Morris et al. | |
| 2014/0282270 A1* | 9/2014 | Slonneger | G06F 3/017 715/863 |
| 2014/0288870 A1 | 9/2014 | Donaldson | |
| 2014/0337791 A1* | 11/2014 | Agnetta | G06F 3/16 715/784 |
| 2015/0046886 A1 | 2/2015 | Goel et al. | |
| 2015/0185837 A1 | 7/2015 | Whitney et al. | |
| 2015/0286285 A1* | 10/2015 | Pantelopoulos | G06F 3/048 345/156 |
| 2015/0301608 A1* | 10/2015 | Nagaraju | G06F 1/1694 345/156 |
| 2016/0018872 A1 | 1/2016 | Tu et al. | |
| 2016/0018900 A1* | 1/2016 | Tu | G06F 1/3218 345/156 |
| 2016/0034143 A1* | 2/2016 | Sharma | G06F 3/0346 715/810 |
| 2016/0034817 A1 | 2/2016 | Ali et al. | |
| 2016/0048161 A1* | 2/2016 | Carceroni | G06F 1/3206 361/679.03 |
| 2016/0051167 A1 | 2/2016 | Saha et al. | |
| 2016/0062515 A1* | 3/2016 | Bae | G06F 3/0416 345/174 |
| 2016/0105619 A1* | 4/2016 | Lee | G06F 3/0482 348/333.01 |
| 2016/0170490 A1 | 6/2016 | Lee | |
| 2016/0202665 A1 | 7/2016 | Park | |
| 2016/0217348 A1* | 7/2016 | Cho | G06V 40/20 |
| 2016/0283783 A1 | 9/2016 | Yang et al. | |
| 2016/0296144 A1 | 10/2016 | Gaddam et al. | |
| 2016/0299570 A1* | 10/2016 | Davydov | G06F 3/167 |
| 2017/0060207 A1* | 3/2017 | Backman | G06F 1/266 |
| 2017/0063767 A1* | 3/2017 | Lukas | H04L 51/42 |
| 2017/0090567 A1 | 3/2017 | Allec et al. | |
| 2017/0108936 A1* | 4/2017 | Feinstein | G06F 3/0346 |
| 2017/0164448 A1* | 6/2017 | Jones | H05B 47/105 |
| 2017/0220122 A1 | 8/2017 | Raffa et al. | |
| 2017/0310673 A1 | 10/2017 | Li et al. | |
| 2018/0188894 A1* | 7/2018 | Feinstein | G06F 3/041 |
| 2018/0239926 A1* | 8/2018 | Momotani | G06F 21/6245 |
| 2018/0246577 A1* | 8/2018 | Bostick | G06F 3/0346 |
| 2018/0307319 A1 | 10/2018 | Karmon et al. | |
| 2018/0332163 A1* | 11/2018 | Park | G06F 3/04842 |
| 2019/0011994 A1 | 1/2019 | Belfiori | |
| 2019/0095814 A1 | 3/2019 | Dubovsky et al. | |
| 2019/0167059 A1* | 6/2019 | Brown | A47L 9/2852 |
| 2020/0150772 A1 | 5/2020 | Quinn et al. | |
| 2020/0301509 A1 | 9/2020 | Liu et al. | |
| 2020/0379573 A1 | 12/2020 | Takahashi | |

\* cited by examiner

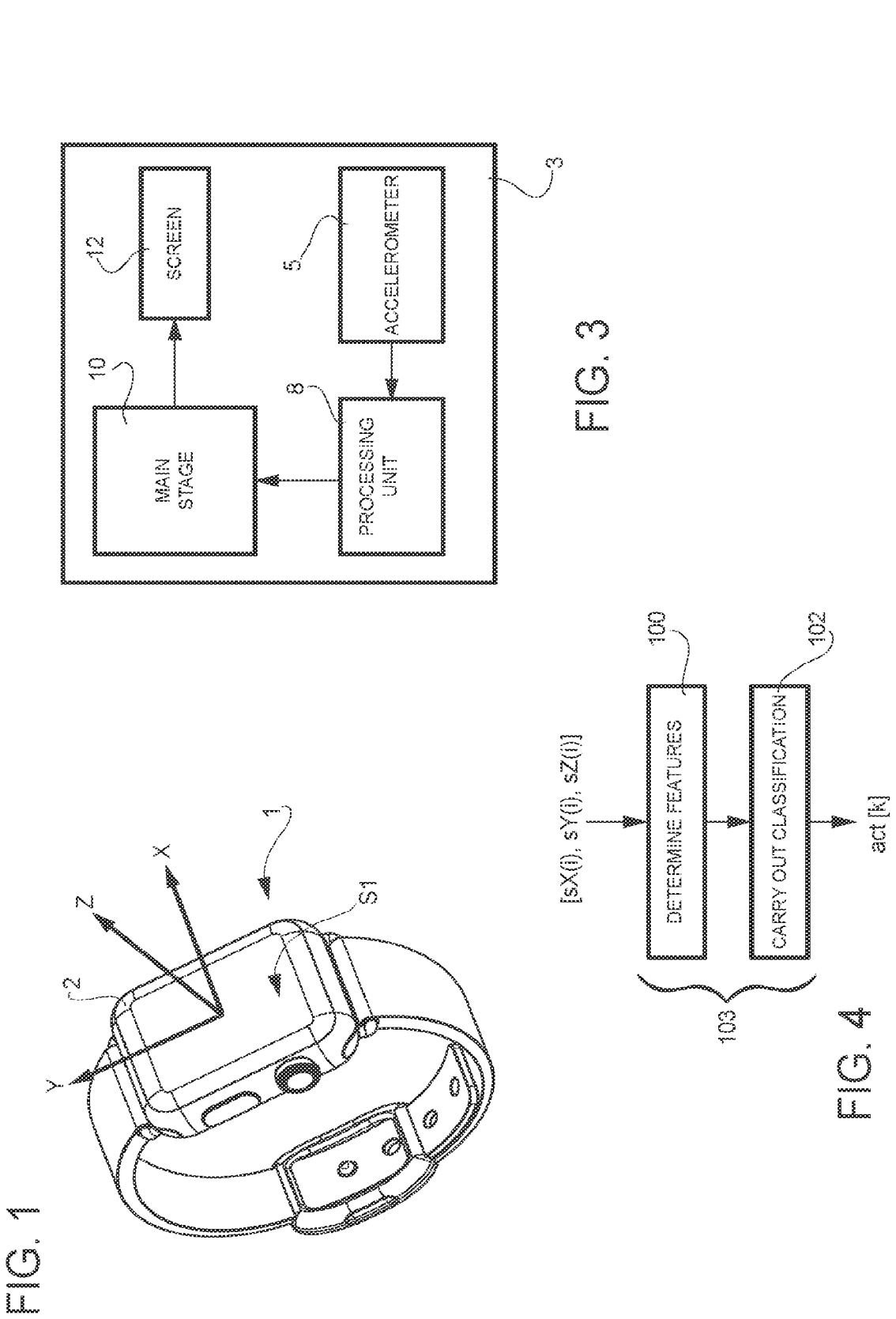

METHOD FOR DETECTING A WRIST-TILT GESTURE AND AN ELECTRONIC UNIT AND A WEARABLE ELECTRONIC DEVICE WHICH IMPLEMENT THE SAME

BACKGROUND

Technical Field

The present disclosure relates to an improved method for detecting a wrist-tilt gesture, for example as an electronic unit and a wearable electronic device which implement said method.

Description of the Related Art

As is known, various wearable electronic devices are available today, such as the so-called "smartbands" or "smartwatches," some of which implement a detection of the movements of the user's wrist, in order to facilitate interaction between the user and the portable electronic device.

In particular, such wearable electronic devices implement the so-called wrist-tilt detection, detection of the wrist-tilt gesture, in order to enable interaction with the electronic device. This detection may be carried out in addition to, or as a replacement of, detection of other actions of the user, such as, for example, pressure exerted on a button. Moreover, following upon detection of the wrist-tilt gesture, such wearable electronic devices perform a corresponding action. For instance, smartwatches are known that switch on the screen following the wrist-tilt detection, so as to minimise power consumption.

In general, it is known that various solutions are possible for the wrist-tilt detection. The solutions that make use of sensors (accelerometers and/or gyroscopes) and dedicated processing units are typically favoured, since they enable reduction of power consumptions required for detection.

For instance, solutions are known that are based upon the analysis of the signals supplied by an accelerometer. Such solutions are characterized by low consumption levels, but also by limited performance (in terms of both latency and of accuracy), in the case where the wearable electronic device is subjected to high accelerations (for example, when the user is running).

According to the above solutions, the wearable electronic device includes a triaxial accelerometer, which in turn supplies electrical signals indicative of the accelerations along three axes of an orthogonal reference system XYZ.

For instance, FIG. 1 shows a smartwatch 1 including an approximately planar body 2 delimited by a pair of main surfaces (one of which is visible in FIG. 1, where it is designated by Si). Moreover, the smartwatch 1 comprises a triaxial accelerometer (not visible in FIG. 1), which is arranged so that the axes X and Y lie in a plane parallel to the main surface Si, thus parallel to the plane of the smartwatch 1, while the axis Z is perpendicular to the latter. For example, when the smartwatch 1 is on the user's wrist (for example, the right wrist), the axis X points in the direction of the arm, instead of the hand.

As illustrated in FIGS. 1, 2a and 2b, a processing unit (not shown in FIG. 1) is present inside the smartwatch 1, which receives the signals generated by the triaxial accelerometer and, by indicating with the signal sY the signal indicative of the acceleration along the axis Y, determines that the wrist-tilt movement has occurred, when it detects i) that the signal sY has exceeded a threshold sY_TH and ii) that, after said threshold has been exceeded, the signal sY remains higher than the threshold sY_TH for at least a threshold period of time $\Delta$ (where $\Delta$ is, for example, 300 ms). This detection mechanism is based upon the fact that, once the user has brought his/her forearm into a position roughly parallel to the ground (and with the wrist facing the user), the projection of the acceleration of gravity along the axis Y, which is initially zero, increases as the user turns his/her wrist so that the smartwatch 1 turns about the axis X, in order to reduce the angle between the axis Y and the gravity vector. For completeness, both FIG. 2a and FIG. 2b also show the signals sX and sZ, which are indicative, respectively, of the accelerations along the axis X and along the axis Z.

FIG. 2a regards a situation in which the user is walking and highlights the correct detection of the wrist-tilt gesture so as to enable interaction with the smartwatch 1. Instead, FIG. 2b regards a situation in which the user is running; this involves the presence of high accelerations, which prevent correct detection of the gesture.

Solutions are likewise known that are based upon analysis of the signals supplied by an accelerometer and by a gyroscope. These solutions are characterized by the capacity of operating properly even in the presence of high accelerations, but also by considerably higher consumption levels.

BRIEF SUMMARY

An embodiment facilitates a method for detecting the wrist-tilt gesture that at least partially overcomes the drawbacks of the prior art.

In an embodiment, a method comprises: receiving an input stream of samples from an accelerometer constrained to an user's wrist, the samples of said input stream being indicative of acceleration values along at least one axis; executing an automatic-learning algorithm on blocks of samples of the input stream of samples to identify, for each block, a corresponding condition of movement of the user, said automatic-learning algorithm being configured so as to identify said corresponding condition of movement from among a plurality of determined conditions of movement; generating a plurality of streams of samples based on the input stream of samples; for each condition of movement identified, selecting a corresponding stream of samples of the plurality of streams of samples and executing a wrist-tilt gesture detection algorithm using samples of the selected stream of the plurality of streams of samples. In an embodiment, said determined conditions of movement comprise at least one condition of rest or walking, and a condition of running; and said generating a plurality of streams of samples comprises: generating a non-filtered stream of samples, equal to at least part of the input stream of samples; and generating a filtered stream of samples by digital low-pass filtering of samples of at least part of the input stream of samples; and said selecting a corresponding stream of samples of the plurality of streams of samples comprises: selecting the non-filtered stream of samples when the condition of rest or walking is identified; and selecting the filtered stream of samples when the running condition is identified. In an embodiment, said executing an automatic-learning algorithm comprises generating, for each block of the input stream of samples, a corresponding value of a classification signal, which is indicative of the condition of movement identified; and wherein the selecting a corresponding stream of samples is executed based on the classification signal. In an embodiment, the executing an automatic-learning algorithm comprises, for each block of samples of the input stream of samples: determining corresponding values of determined features of the block of samples of the input stream of samples; and executing a classification algorithm based on said corresponding values of determined features. In an embodiment, said determined features of the block of samples of the input stream of samples are chosen from among: variance, maximum or minimum of the block of samples of the input stream of samples, or of the Euclidean norms of the samples of said block of samples of the input stream of samples, or various combinations thereof. In an embodiment, the executing a wrist-tilt gesture detection algorithm comprises detecting whether the selected stream of samples exceeds a signal threshold for a threshold duration period. In an embodiment, the executing a wrist-tilt gesture detection algorithm comprises varying at least one parameter of said wrist-tilt detection algorithm based on the condition of movement identified. In an embodiment, said at least one parameter is a signal threshold or a duration threshold. In an embodiment, the method comprises, for each condition of movement identified, selecting one of a first wrist-tilt gesture detection algorithm and at least a second wrist-tilt gesture detection algorithm, based on the condition of movement identified; and said executing a wrist-tilt gesture detection algorithm comprises executing the selected wrist-tilt gesture detection algorithm. In an embodiment, the method comprises: based on said input stream of samples from the accelerometer, determining whether an arm of the user to which the accelerometer is constrained is tilted from a gravity direction by an angle which is less than or equal to an angle threshold; and if said arm is tilted from the gravity direction by an angle which is higher than said angle threshold, carrying out said steps of executing an automatic-learning algorithm, generating a plurality of streams of samples to be analysed, selecting, for each condition of movement identified, a corresponding stream of samples to be analysed and executing said wrist-tilt gesture detection algorithm; or alternatively if said arm is tilted from the gravity direction by an angle which is lower than or equal to said angle threshold, receiving a signal from a gyroscope constrained to the user's wrist and detecting occurrence of a wrist-tilt gesture based on said signal from the gyroscope.

In an embodiment, an electronic device comprises: an input, which, in operation, receives an input stream of accelerometer data samples indicative of acceleration values along at least one axis; and circuitry, coupled to the input, wherein the circuitry, in operation: executes an automatic-learning algorithm on blocks of samples of the input stream of accelerometer data samples to identify, for each block, a corresponding condition-of-user-movement from among a plurality of determined conditions-of-user-movement; generates a plurality of streams of samples based on the input stream of accelerometer data samples; for each condition of movement identified, selects a corresponding stream of samples of the plurality of streams of samples and executes a wrist-tilt gesture detection algorithm using samples of the selected stream of the plurality of streams of samples. In an embodiment, said determined conditions-of-user-movement comprise at least one condition of rest or walking, and a condition of running; and wherein the circuitry: generates the plurality of streams of samples by: generating a non-filtered stream of samples, equal to at least part of the input stream of samples; and generating a filtered stream of samples by digital low-pass filtering of samples of at least part of the input stream of samples; and selects a corresponding stream of samples of the plurality of streams of samples by: selecting the non-filtered stream of samples when the condition of rest or walking is identified; and selecting the filtered stream of samples when the running condition is identified. In an embodiment, the circuitry, in operation, generates, for each block of the input stream of accelerometer data samples, a corresponding value of a classification signal, which is indicative of the condition-of-user-movement identified; and selects the corresponding stream of samples based on the classification signal. In an embodiment, the circuitry, in operation: determines corresponding values of determined features of a block of samples of the input stream of samples; and executes a classification algorithm based on said corresponding values of determined features. In an embodiment, the circuitry, in operation, detects whether the selected stream of samples exceeds a signal threshold for a threshold period of time. In an embodiment, the circuitry, in operation, varies at least one parameter of the wrist-tilt gesture detection algorithm based on the condition-of-user-movement identified. In an embodiment, the circuitry, in operation: selects, for each condition of movement identified, one of a first wrist-tilt gesture detection algorithm and at least a second wrist-tilt gesture detection algorithm based on the condition-of-user-movement identified; and executes the selected wrist-tilt gesture detection algorithm. In an embodiment, the electronic device comprises a second input, which, in operation, receives a gyroscope signal, wherein the circuitry is coupled to the second input and the circuitry, in operation, determines whether said input stream of accelerometer data samples indicates a tilt from a gravity direction by an angle which exceeds an angle threshold; if said input stream of accelerometer data samples indicates a tilt from the gravity direction by an angle which is higher than said angle threshold, executes said wrist-tilt gesture detection algorithm based on the selected stream of samples; and if said input stream of accelerometer data samples indicates a tilt lower than or equal to said angle threshold, detects an occurrence of a wrist-tilt gesture based on the gyroscope signal.

In an embodiment, a system comprises: an accelerometer, which, in operation, generates a stream of accelerometer data samples indicative of acceleration values along at least one axis; and circuitry, coupled to the accelerometer, wherein the circuitry, in operation: executes an automatic-learning algorithm on blocks of accelerometer data samples to identify, for each block, a corresponding condition-of-user-movement from among a plurality of determined conditions-of-user-movement; generates a plurality of streams of samples based on accelerometer data samples of the stream of accelerometer data samples; for each condition of movement identified, selects a corresponding stream of samples of the plurality of streams of samples and executes a wrist-tilt gesture detection algorithm using samples of the selected stream of the plurality of streams of samples to generate a wrist-tilt detection signal. In an embodiment, the system comprises: a screen, wherein the circuitry, in operation controls the screen based on the wrist-tilt detection signal. In an embodiment, the system comprises: a gyroscope coupled to the circuitry, wherein the gyroscope, in operation, generates a gyroscope signal. In an embodiment, the system comprises a screen coupled to the circuitry, wherein the circuitry, in operation, determines whether the stream of accelerometer data samples indicates a tilt from a gravity direction by an angle which exceeds an angle threshold; in response to said stream of accelerometer data samples indicating a tilt from the gravity direction by an angle which is higher than said angle threshold, controls the screen based on the wrist-tilt detection signal; and in response to said stream of accelerometer data samples indicating a tilt lower than or equal to said angle threshold, detects an occurrence of a wrist-tilt gesture based on the gyroscope signal. In an embodiment, the system comprises a wearable device including the accelerometer and the circuitry.

In an embodiment, a non-transitory computer-readable medium's contents configure circuitry of a wearable device to perform a method, the method comprising: executing an automatic-learning algorithm on blocks of accelerometer data samples to identify, for each block, a corresponding condition-of-user-movement from among a plurality of determined conditions-of-user-movement; generating a plurality of streams of samples based on accelerometer data samples of the stream of accelerometer data samples; for each condition of movement identified, selecting a corresponding stream of samples of the plurality of streams of samples and executing a wrist-tilt gesture detection algorithm using samples of the selected stream of the plurality of streams of samples to generate a wrist-tilt detection signal. In an embodiment, the contents comprises instructions executed by the circuitry. In an embodiment, the method comprises: determining whether the stream of accelerometer data samples indicates a tilt from a gravity direction by an angle which exceeds an angle threshold; in response to said stream of accelerometer data samples indicating a tilt from the gravity direction by an angle which is higher than said angle threshold, generating a control signal based on the wrist-tilt detection signal; and in response to said stream of accelerometer data samples indicating a tilt lower than or equal to said angle threshold, generating the control signal based on a gyroscope signal.

BRIEF DESCRIPTION OF THE SEVERAL VIEWS OF THE DRAWINGS

For a better understanding of the present disclosure, example embodiments will now be described, purely by way of non-limiting example, with reference to the attached drawings, wherein:

FIG. 1 is a perspective view of a wearable electronic device;

FIG. 3 shows a block diagram of an embodiment of a wearable electronic device;

FIGS. 4 and 6 show flowcharts of embodiments of operations performed by a processing unit of the wearable electronic device, such as the device illustrated in FIG. 3;

DETAILED DESCRIPTION

Figures 2A, 2B:
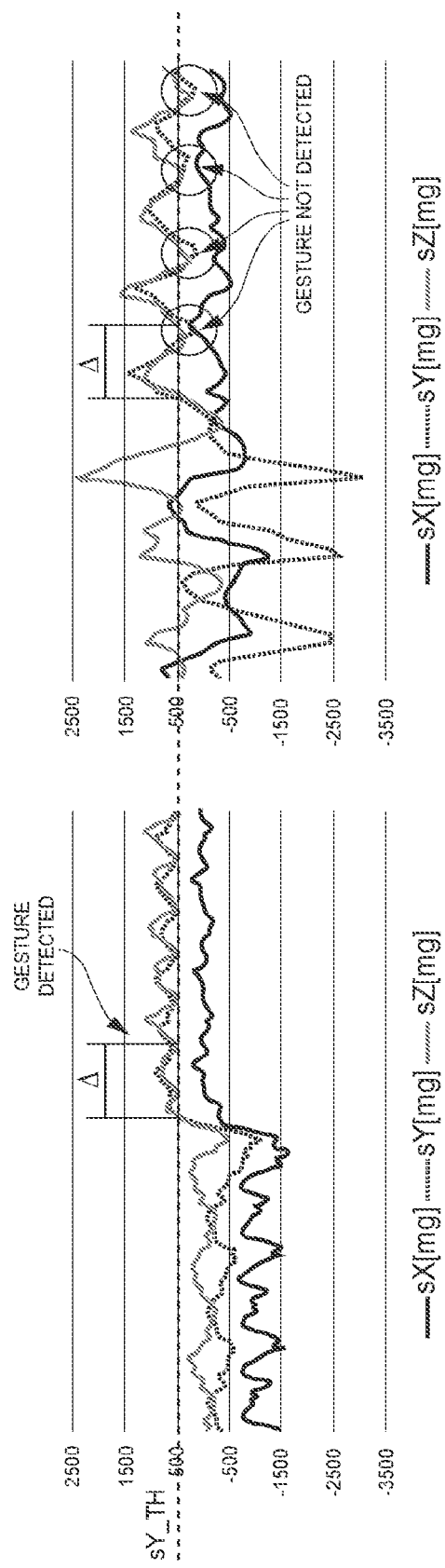
FIGS. 2a and 2b show time plots of signals indicative of accelerations generated by a triaxial accelerometer constrained to the wrist of a user, when the user is walking and when he/she is running, respectively.

In what follows, the present method is described with reference, by way of example, to the implementation thereof by a wearable electronic device 3.

As illustrated in FIG. 3, the wearable electronic device 3 comprises: a triaxial accelerometer 5; a processing unit 8; a main stage 10; and a screen 12. Purely by way of example, the wearable electronic device 3 has the same body 2 as that shown in FIG. 1, and the main surface Si coincides with the surface of the screen 12. The orientation of the axes XYZ of the accelerometer 5 is the same as the one illustrated in FIG. 1.

The accelerometer 5 is coupled to the processing unit 8 so as to supply to the latter electrical signals indicative of the values of the accelerations along the axes X, Y, and Z, measured by the accelerometer 5. The processing unit 8 therefore receives, with a frequency for example of twenty-five samples per second, acceleration samples measured by the accelerometer 5. Each sample may consist of a triad of acceleration values, corresponding to the axes X, Y, and Z, respectively.

In an embodiment, the processing unit 8 executes the operations illustrated in FIG. 4, where the samples are designated by $[sX(i), sY(i), sZ(i)]$, where "i" is a progressive integer.

In detail, the processing unit 8 processes blocks (sets) of acceleration samples, each of which is formed by the acceleration samples generated by the accelerometer 5 during a corresponding time window having a duration, for example, of one second. Purely by way of example, and without this implying any loss of generality, the time windows are one after another; therefore, successive blocks of acceleration samples do not overlap each other; they do not have samples in common.

This having been said, the processing unit 8 determines (block 100), for each block of samples, the corresponding values of a number of determined features, chosen, for example, from among: the mean, the minimum, the maximum, and the variance of the acceleration samples of the block, or of Euclidean norms of the acceleration samples of the block. The determined features may be predetermined.

Next, the processing unit 8 executes (block 102), for each block of samples, a classification algorithm, on the basis of the corresponding values of the determined features.

In particular, the processing unit 8 is configured to implement an automatic machine-learning algorithm, such as, for example, a decision tree, a support-vector machine (SVM), or a neural network. In greater detail, this algorithm is a classification algorithm, typically previously trained, so as to provide, for each block of samples, an indication of the fact that the block of samples has been generated while the user, to whose wrist the wearable electronic device 3 had previously been constrained, i) was stationary (at rest), ii) was walking, or iii) was running. In practice, in this embodiment, the output classes of the classification algorithm are three and refer to three conditions of movement of the user who is wearing the wearable electronic device 3. For this purpose, the aforementioned determined features characterize the classes that must be recognized by the classification algorithm.

In order to operate in the way described, a training step is carried out to define the classification algorithm. For instance, the training may be of the so-called supervised type and comprising acquiring a plurality of sequences of training samples, for example by getting different users to wear the wearable electronic device 3, in different (known) conditions of movement so as to acquire a plurality of blocks of training samples, generated during corresponding training time windows that had a duration equal to the duration of the aforementioned time window and during which the user was in a known condition from among the aforementioned three conditions of movement.

In greater detail, the training has been carried out, for example, with the aid of a computer, which has stored the associations between each block of training samples and the corresponding known condition of movement. In addition, for each block of training samples, the computer has determined the corresponding values of said determined features. Finally, through the use of an automatic-learning algorithm of a per se known type, the computer has trained the classification algorithm on the basis of the values of the determined features of the blocks of training samples and of the corresponding known conditions of movement.

Once again with reference to use after the training step, and therefore with reference to the situation in which the wearable electronic device 3 is worn by a user whose condition of movement is not known, the operations referred to in block 102 enable determination, for each block of samples, of a corresponding value of a signal act[k] (where k is an integer that indicates the block), which is indicative of the corresponding condition of movement identified; act[k] may, for example, be alternatively equal to zero, one or two, if the condition of movement identified by the classification algorithm is "stationary," "walking" or "running," respectively.

In what follows, the operations of blocks 100 and 102 are referred to, as a whole, as operations of identification of the condition of movement (block 103). In addition, further operations performed by the processing unit 8 are described with reference to the representation of FIG. 5, where the operations are illustrated in the form of corresponding stages of an example of equivalent digital circuit implemented via software by the processing unit 8. The connections between the various stages illustrated in FIG. 5, and also the number of stages, are to be understood as being purely provided by way of example; moreover, as mentioned, the algorithm may be executed either totally or in part via software.

This having been said, the processing unit 8 implements a first filtering stage, a second filtering stage and a third filtering stage, respectively designated by 110, 112, 114, which operate on the acceleration samples [sX(i), sY(i), sZ(i)], which, in turn, represent a stream of input samples.

The first filtering stage 110 filters the stream of the acceleration samples [sX(i), sY(i), sZ(i)] by implementing a first digital filter so as to obtain a first filtered stream of samples [sX(i)', sY(i)', sZ(i)']. The second filtering stage 112 filters the stream of the acceleration samples [sX(i), sY(i), sZ(i)] by implementing a second digital filter so as to obtain a second filtered stream of samples [sX(i)'', sY(i)'', sZ(i)'']. The third filtering stage 114 filters the stream of the acceleration samples [sX(i), sY(i), sZ(i)] by implementing a third digital filter so as to obtain a third filtered stream of samples [sX(i)''', sY(i)''', sZ(i)'''].

In greater detail, each of the aforementioned first, second, and third filtering stages 110, 112, 114 operates independently on the three substreams formed by the elements corresponding, respectively, to the axes X, Y, and Z of the acceleration samples [sX(i), sY(i), sZ(i)].

In addition, the processing unit 8 implements a selection stage 122, which selects one from among the first, second, and third filtered streams of samples, as a function of the value of the signal act[k], and therefore on the basis of the condition of movement identified by the classification algorithm. In other words, corresponding to identification, in the course of the operations of block 103, of each of the three conditions of movement is the selection of a corresponding filtered stream of samples, referred to briefly hereinafter as the selected stream of samples.

Furthermore, the processing unit 8 implements a first gesture-detection stage 124, which receives at input the selected stream of samples and generates an output signal sOUT, which is indicative of the detection of the wrist-tilt gesture.

The first gesture-detection stage 124 may be of a type in itself known. Described hereinafter is an example of operation of the first gesture-detection stage 124, with reference to the ensuing scenario.

In detail, it is assumed that the first filtering stage 110 does not carry out any filtering, so that the first filtered stream of samples [sX(i)', sY(i)', sZ(i)'] coincides with the stream of the acceleration samples [sX(i), sY(i), sZ(i)]. Once again by way of example, it is likewise assumed that the second filtering stage 112 is absent; in other words, it is assumed that the processing unit 8 determines a number of filtered streams of samples lower than the number of possible conditions of movement that can be identified by the classification algorithm. It is moreover assumed that the third filtering stage 114 implements a low-pass IIR filter, for example a first-order and of a Butterworth type, with a cut-off frequency of, for example, 1 Hz. Finally, it is assumed that, when act[k] is equal to zero or to one, when the condition of movement identified by the classification algorithm is "stationary" or "walking," respectively, the selection stage 122 selects the first filtered stream of samples, which, as mentioned previously, coincides with the stream of the acceleration samples [sX(i), sY(i), sZ(i)]; instead, when act[k] is equal to two, when the condition of movement identified by the classification algorithm is "running," the selection stage 122 selects the third filtered stream of samples [sX(i)''', sY(i)''', sZ(i)'''], which represents a low-pass filtered version of the stream of the acceleration samples [sX(i), sY(i), sZ(i)], therefore with linear accelerations (understood as accelerations additional to the acceleration of gravity) reduced with respect to the latter. In other words, the first gesture-detection stage 124 receives in succession non-filtered portions and filtered portions of the stream of the acceleration samples [sX(i), sY(i), sZ(i)] generated by the accelerometer 5, which are analysed by the first gesture-detection stage 124 in order to detect whether the wrist-tilt gesture has been performed. Equivalently, the operations of block 103 and the selection stage 122 discriminate only between two conditions of movement: a condition of rest or walking, and a condition of running.

Figure 6:
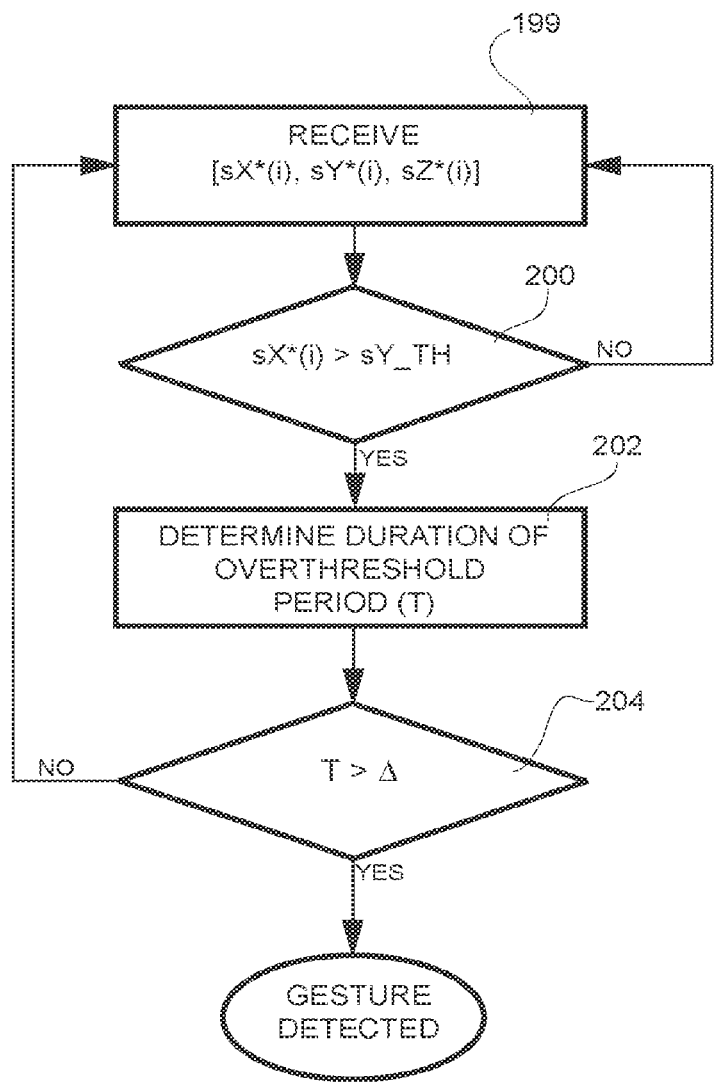

In detail, the first gesture-detection stage 124 executes the operations illustrated in FIG. 6, where the selected stream of samples is designated by [sX*(i), sY*(i), sZ*(i)]].

In particular, the first gesture-detection stage 124 receives (block 199) the samples of the selected stream [sX*(i), sY*(i), sZ*(i)] and, for each element sY*(i) of the selected stream of samples [sX*(i), sY*(i), sZ*(i)], detects (block 200) whether it exceeds a threshold sY_TH (output YES from block 200) otherwise (output NO from block 200), it analyses the next element sY*(i+1).

When the first gesture-detection stage 124 detects that an element sY*(j) exceeds the threshold sY_TH, it determines (block 202) the duration of an over-threshold period T, where the values of the successive elements sY*(m) (with m>j) are higher than the threshold sY_TH. Next, the first gesture-detection stage 124 checks (block 204) whether the duration of the over-threshold period T exceeds a threshold period of time Δ (output YES from block 204), in which case it sets the output signal sOUT so that it will indicate that the wrist-tilt gesture has been detected, otherwise (output NO from block 204), the operations of block 199 are carried out again.

In practice, the processing unit 8 selects each time, on the basis of the condition of movement identified, the most favourable stream of samples on which to carry out the wrist-tilt detection algorithm. In particular, with reference to the example proposed, when the user is stationary or in any case he/she is not running, and therefore in the presence of low linear accelerations, the wrist-tilt detection algorithm is carried out directly on the samples of the stream of the acceleration samples [sX(i), sY(i), sZ(i)] generated by the accelerometer 5; instead, when the user is running, and therefore in the presence of high linear accelerations that affect the acceleration values measured by the accelerometer 5, the wrist-tilt detection algorithm is executed on a low-pass filtered version of the samples of the stream of the acceleration samples [sX(i), sY(i), sZ(i)] generated by the accelerometer 5, therefore on a version less affected by the aforementioned linear accelerations. In this way, an optimal detection of a possible event of wrist tilting may be facilitated, without introducing undesired delays and without having to resort to additional sensors. Switching between the streams of the samples on which the wrist-tilt detection algorithm is carried out (also referred to briefly as streams of samples to be analysed) can occur following upon variations of the value of the signal act[k].

Figure 5:
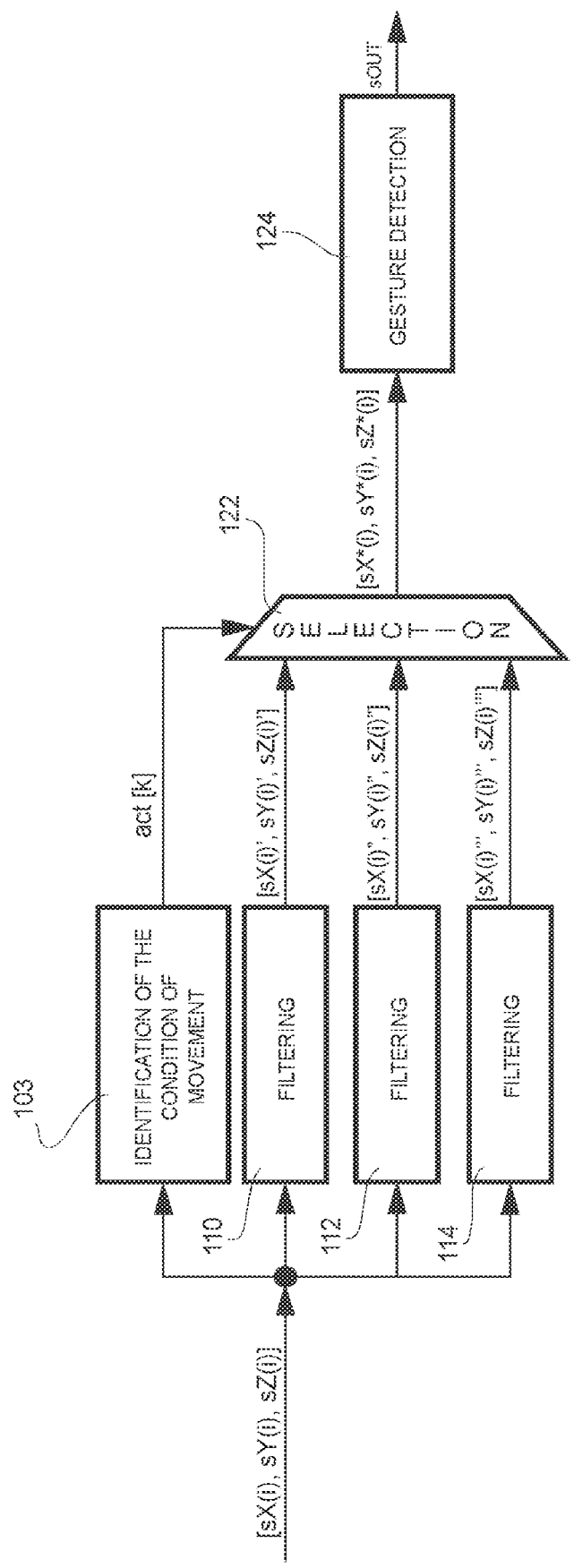
FIGS. 5, 7, and 8 show block diagrams of embodiments of equivalent digital circuits, which may implement operations performed by the processing unit of the wearable electronic device illustrated in FIG. 3.

Even though not mentioned explicitly previously, and without this implying any loss of generality, the operations illustrated in FIG. 5 envisage that the signal act[k], once it has assumed a respective value following upon execution of the operations of identification of the condition of movement (block 103) on a first block of samples, maintains said value until the operations of identification of the condition of movement are executed on a second block of samples. It is moreover found that the first gesture-detection stage 124 receives, at input, samples that have been selected by the selection stage 122 on the basis of the values of the acceleration samples [sX(i), sY(i), sZ(i)] of previous blocks. It is, however, possible to implement variants that, for example, make use of buffers (not illustrated) and enable variation of the temporal relations present between the signal act[k] and, for example, the filtered streams of samples.

Figure 7:
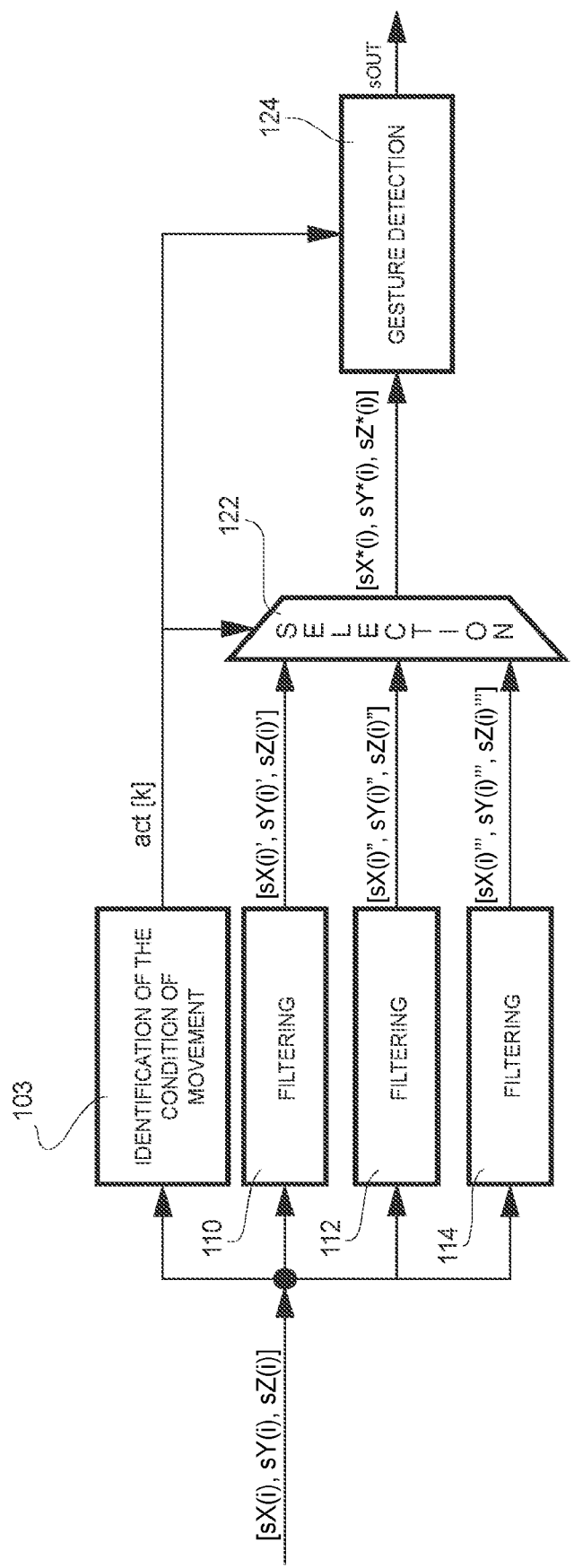

As illustrated in FIG. 7, moreover possible are variants in which the first gesture-detection stage 124 includes parameters (for example, the value of the threshold sY_TH and/or the duration of the threshold period A) that dynamically depend upon the value of the signal act[k]; they are updated as a function of the values progressively assumed by the signal act[k].

Figure 8:
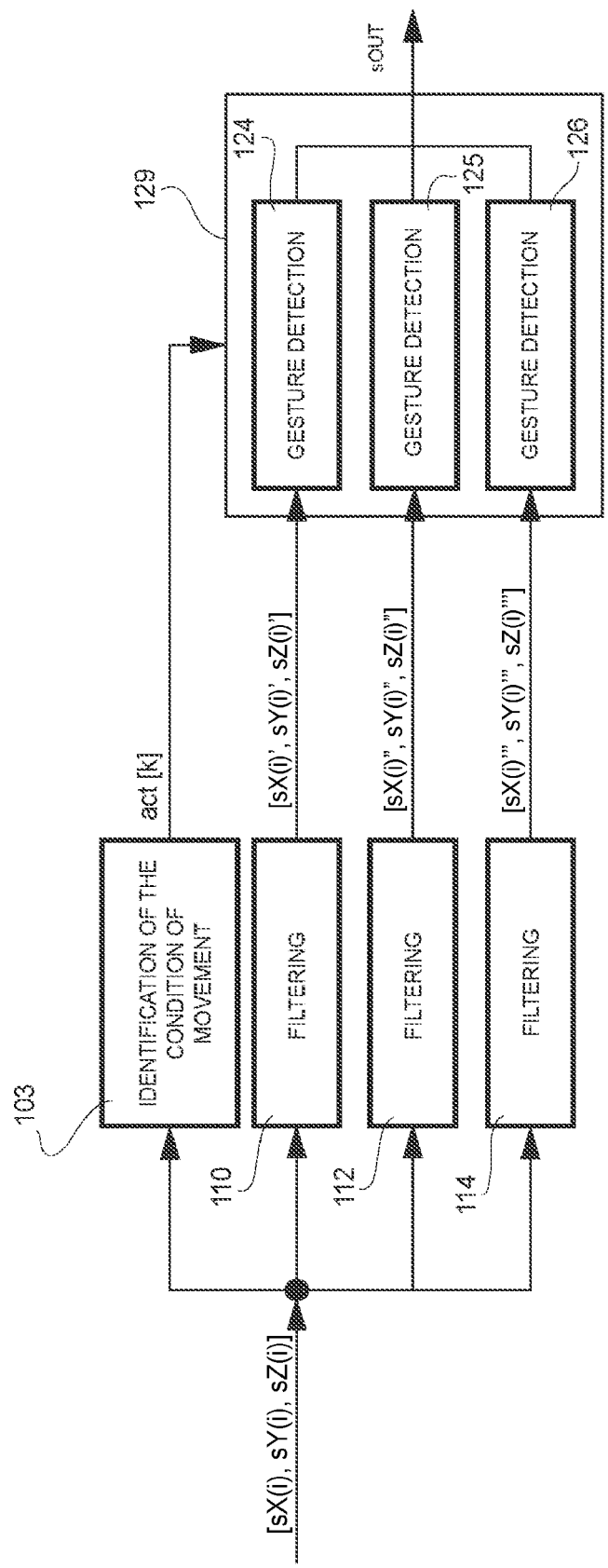

As shown in FIG. 8, variants are moreover possible in which the processing unit 8 implements further gesture-detection stages, additional to the first gesture-detection stage 124; for example, the embodiment illustrated in FIG. 8 also envisages a second gesture-detection stage 125 and a third gesture-detection stage 126, which form, together with the first gesture-detection stage 124, an output stage 129, controlled by the signal act[k] and adapted to receive at input the first, second, and third filtered streams of samples [sX(i)', sY(i)', sZ(i)'], [sX(i)'', sY(i)'', sZ(i)''], and [sX(i)''', sY(i)''', sZ(i)'''].

In this case, the selection stage 122 is absent since selection of the filtered stream of samples is executed by the output stage 129. Moreover, the first, second, and third gesture-detection stages 124, 125, 126 receive at input, respectively, the first, second, and third filtered streams of samples [sX(i)', sY(i)', sZ(i)'], [sX(i)'', sY(i)'', sZ(i)''] and [sX(i)''', sY(i)''', sZ(i)''']. Moreover, the first, second, and third gesture-detection stages 124, 125, 126 are configured to implement different gesture-detection algorithms.

In greater detail, each one of the first, second, and third gesture-detection stages 124, 125, 126 is associated with a different possible value of the signal act[k]. In addition, the output signal sOUT is generated each time by the gesture-detection stage associated with the value of the signal act[k]. In this way, it is possible to optimize not only the parameters of the gesture-detection algorithm, but also the type of gesture-detection algorithm, on the basis of the condition of movement identified by the operations of block 103.

Once again with reference to FIG. 3, the processing unit 8 sends the output signal sOUT to the main stage 10, which may, for example, control switching-on of the screen 12 when the wrist-tilt gesture is detected.

The advantages that the present detection method affords emerge clearly from the foregoing description. In particular, this method enables both a low latency when the user is stationary or in any case is walking slowly, and a high accuracy when the user is running, without any need to resort to components characterized by high power consumption, such as gyroscopes.

Finally, it is clear that modifications and variations may be made to what has been described and illustrated herein, without thereby departing from the scope of the present disclosure.

For instance, the gesture-detection algorithm may be different from what has been described and may, for example, envisage processing of the accelerometric signals corresponding also to the axes X and Z. Likewise, the number and type of the possible conditions of movement may be different from what has been described; for example, it is possible for the operations of block 103 to enable identification also of conditions in which the user does not have an upright posture, but is lying down.

As mentioned previously, it is moreover possible for the streams to be analysed, namely, the filtered streams of samples, not to be generated entirely. In fact, it is possible for only the samples of the filtered stream of samples indicated by the signal act[k] to be generated, therefore leaving the filtering stages not involved in this operation temporarily inactive, in order to prevent generation of samples that will not be analysed by the gesture-detection stage/stages.

It is possible for the processing unit 8, instead of being separate from the accelerometer 5, to be integrated in the latter, for example within an ASIC (not illustrated) that, among other things, generates the initial stream of samples [sX(i), sY(i), sZ(i)]. Once again by way of example, it is possible for the processing unit 8 to be implemented by the main stage 10.

Finally, it is possible for at least part of the stages described previously to be formed by dedicated hardware components, instead of being implemented via software.

Figure 9B:
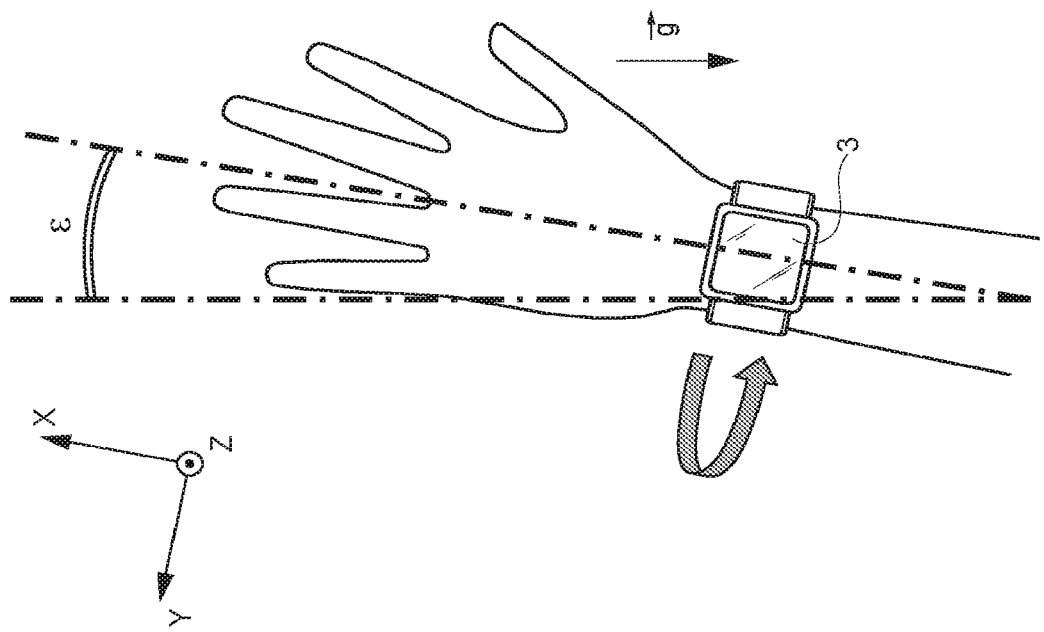
FIGS. 9A and 9B show perspective views of an arm, a hand and a wrist wearing embodiments of a wearable electronic device.
Figure 9A:
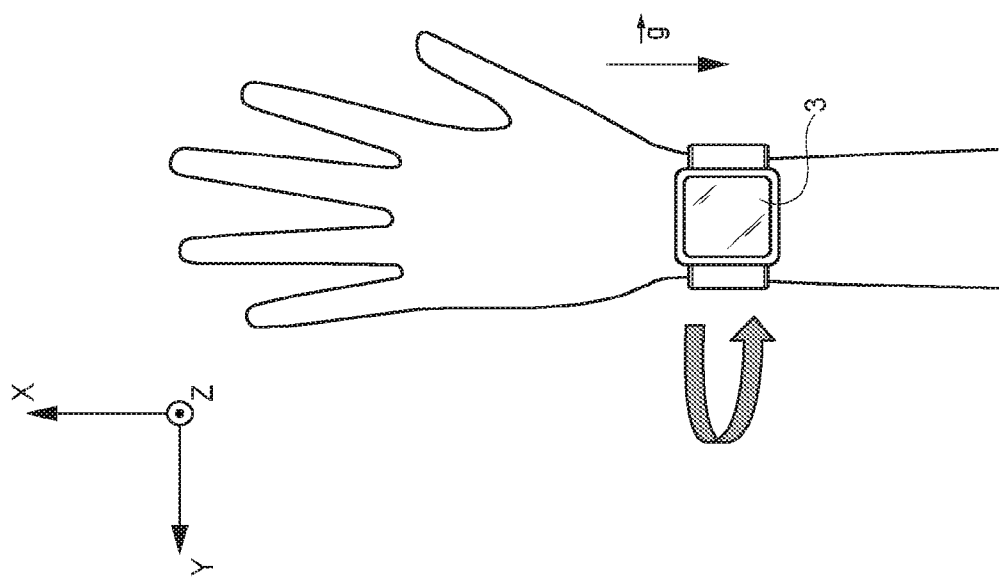

In addition, further embodiments are possible, which may turn out to be suitable to applications in which the user may happen to keep his arm parallel to the gravity direction, as shown as an example in FIG. 9A, wherein the gravity direction is designated by g; in this case, the rotation of the wrist about the axis X does not cause any change of the projection of the acceleration of gravity along the axis Y, which stays equal to zero.

Figure 10:
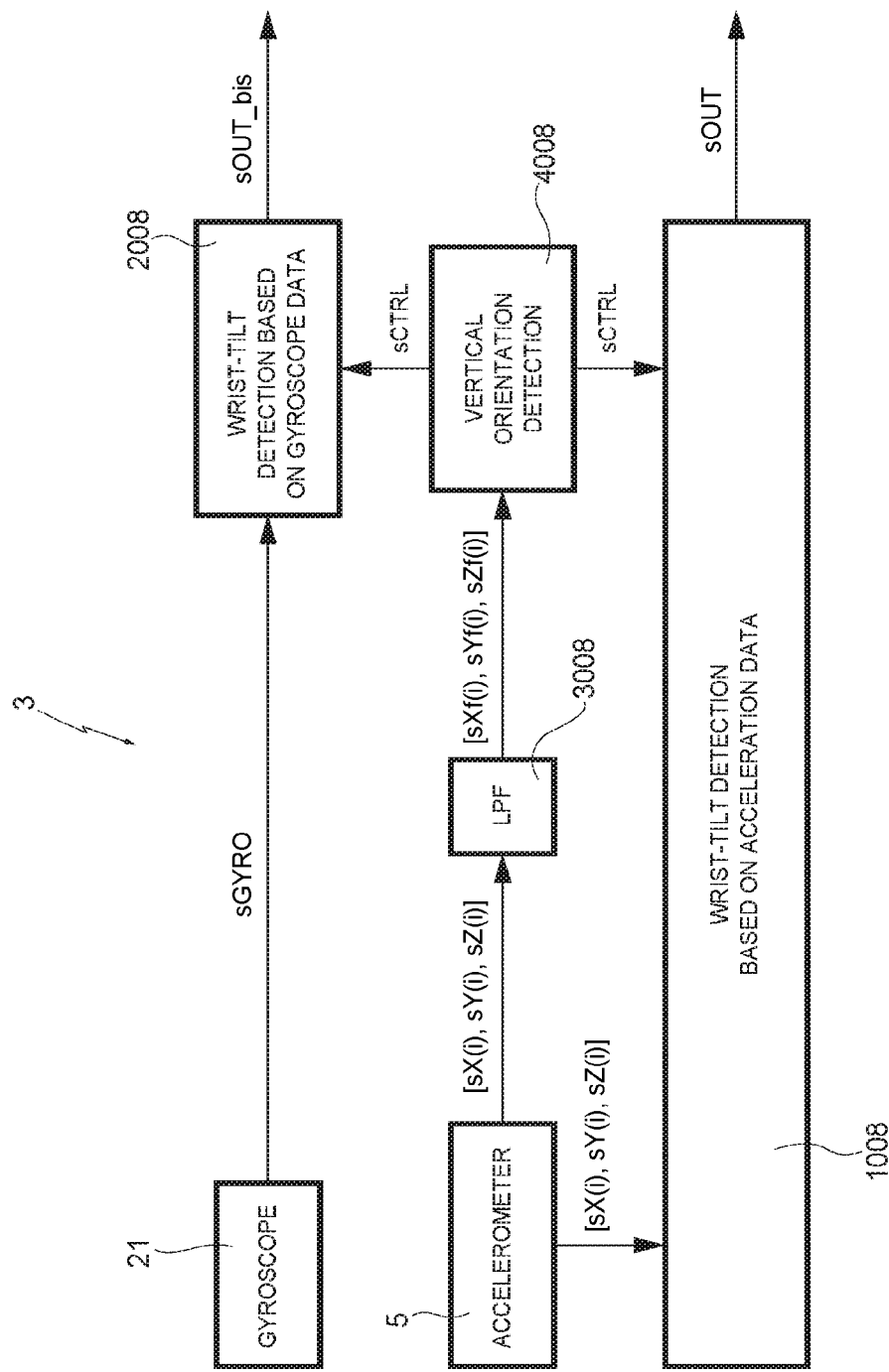
FIG. 10 shows a block diagram of an embodiment of a wearable electronic device.

In detail, as shown in FIG. 10, the wearable electronic device 3 comprises a gyroscope 21, which operates in a per se known manner. In particular, the gyroscope 21 is fixed with respect to the accelerometer 5, with which it shares the abovementioned axes X,Y,Z; in addition, in a per se known manner, the gyroscope 21 generates a corresponding signal sGYRO.

In addition, the processing unit 8 performs a first group of operations, which are shown as a whole as a block 1008, labelled as "wrist-tilt detection based on acceleration data." In particular, these operations, carried out starting from the samples [sX(i), sY(i), sZ(i)] provided by the accelerometer 5, may be the same as the ones described with reference to any of the previous embodiments (any of FIG. 5, 7 or 8), so as to generate the output signal sOUT.

In addition, the processing unit 8 performs a second group of operations 2008, which are shown as a whole as a block 2008, labelled as "wrist-tilt detection based on gyroscope data." In particular, these operations are carried out starting from the signal sGYRO and lead to the generation, in a per se known manner, of a secondary output signal sOUT bis, which is indicative of the occurrence of a wrist-tilt.

As an example, the signal sGYRO may comprise a sequence of corresponding samples [GyrX(u), GyrY(u), GyrZ(u)] (with u integer positive), wherein GyrX(u), GyrY(u), GyrZ(u) indicate the angular rates respectively sensed along the X, Y and Z axes. In this case, the second group of operations 2008 may comprise comparing the samples GyrX(u) to a corresponding value threshold, so as to verify whether the samples GyrX(u), after overcoming said value threshold, stay above the threshold for time at least equal to a corresponding duration threshold, in which case the secondary output signal BOUT bis indicates that a wrist-tilt has occurred. As an alternative, the second group of operations 2008 may comprise integrating the samples GyrX(u) and detecting the occurrence of a wrist-tilt when the value of the integral overcomes a corresponding threshold (e.g., equal to 30°), in which case the secondary output signal sOUT bis indicates the occurrence of a wrist-tilt.

In addition, the processing unit 8 carries out a third group of operations, which includes carrying out (block 3008) a low pass filtering of the samples [sX(i), sY(i), sZ(i)] provided by the accelerometer 5, so as to generate an additional filtered stream of samples [sXf(i), sYf(i), sZf(i)]. In addition, the third group of operations includes determining (block 4008), based on the additional filtered stream of samples [sXf(i), sYf(i), sZf(i)], whether the longitudinal axis of the arm is approximately parallel to the gravity direction (e.g., such as in FIG. 9A). In particular, by designating by c the angle between the gravity direction and the longitudinal axis of the arm, the third group of operations (block 4008) comprises determining whether the modulus of the angle c is lower than or equal to an additional angle threshold equal to, e.g., 20° (e.g., as shown in FIG. 9B).

In addition, the third group of operations (block 4008) includes generating a control signal sCTRL, indicative of whether the modulus of the abovementioned angle c is lower than or equal to the abovementioned additional angle threshold. The control signal sCTRL controls the functioning of blocks 1008 and 2008.

In particular, if the control signal sCTRL indicates that the modulus of the abovementioned angle c is higher than the additional angle threshold, then the operations of block 1008 are performed, and the operations of block 2008 are halted, so that only the output signal sOUT is provided to the main stage 10; on the contrary, if the control signal sCTRL indicates that the modulus of the abovementioned angle c is lower than or equal to the additional angle threshold, then the operations of block 2008 are performed, and the operations of block 1008 are halted, so that only the additional output signal sOUT bis is provided to the main stage 10, which may operate in the same way as described before.

In this way, the processing unit 8 carries out the wrist-tilt detection algorithm which best fits the current orientation of the arm.

In addition, although not shown, if the control signal sCTRL indicates that the modulus of the abovementioned angle c is higher than the additional angle threshold, then processing unit 8 may turn off the gyroscope 21, which will be turned on only when the control signal sCTRL indicates that the modulus of the abovementioned angle c is lower than or equal to the additional angle threshold, so as to save power.

In a per se known manner, in that concerns the operations of block 4008, the processing unit 8 may determine that the arm is arranged approximately vertically (the angle c is lower than or equal to the additional angle threshold), and set the value of the control signal sCTRL accordingly, if each of the moduli of the values of sYf(i), sZf(i) is lower than or equal to a first orientation threshold, and:

the value of sXf(i) is greater than a positive second orientation threshold, if the wearable electronic device 3 is worn on the left wrist; or the value of sXf(i) is lower than or equal to a negative second orientation threshold if the wearable electronic device 3 is worn on the right wrist.

Some embodiments may take the form of or comprise computer program products. For example, according to one embodiment there is provided a computer readable medium comprising a computer program adapted to perform one or more of the methods or functions described above. The medium may be a physical storage medium, such as for example a Read Only Memory (ROM) chip, or a disk such as a Digital Versatile Disk (DVD-ROM), Compact Disk (CD-ROM), a hard disk, a memory, a network, or a portable media article to be read by an appropriate drive or via an appropriate connection, including as encoded in one or more barcodes or other related codes stored on one or more such computer-readable mediums and being readable by an appropriate reader device.

Furthermore, in some embodiments, some or all of the methods and/or functionality may be implemented or provided in other manners, such as at least partially in firmware and/or hardware, including, but not limited to, one or more application-specific integrated circuits (ASICs), digital signal processors, discrete circuitry, logic gates, standard integrated circuits, controllers (e.g., by executing appropriate instructions, and including microcontrollers and/or embedded controllers), field-programmable gate arrays (FPGAs), complex programmable logic devices (CPLDs), etc., as well as devices that employ RFID technology, and various combinations thereof. The various embodiments described above can be combined to provide further embodiments. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method, comprising:
receiving an input stream of accelerometer data samples from an accelerometer, the samples of the input stream of accelerometer data samples being indicative of acceleration values along a plurality of axes of a wearable device;

based on the input stream of accelerometer data samples, determining a tilt angle of an axis of the plurality of axes of the wearable device with respect to a gravity direction;

comparing the determined tilt angle to an angle threshold;

selecting a type of data to be used to detect wrist-tilt gestures based on the comparing;

in response to selecting gyroscope data as the type of data to be used to detect wrist-tilt gestures, detecting occurrence of a wrist-tilt gesture based on a set of samples of gyroscope data; and in response to selecting accelerometer data as the type of data to be used to detect wrist-tilt gestures:

executing an automatic-learning algorithm on blocks of samples of the input stream of accelerometer data samples to identify, for each block, corresponding conditions-of-user-movement from among a plurality of determined conditions-of-user-movement;

generating a plurality of two or more-streams of accelerometer data samples based on the input stream of accelerometer data samples, the plurality of streams of accelerometer data samples including a filtered stream of accelerometer data samples;

selecting a stream of accelerometer data samples of the plurality of streams of accelerometer data samples based on an identified condition of user movement; and executing a wrist-tilt gesture detection algorithm using samples of the selected stream of the plurality of streams of samples of accelerometer data samples.

2. The method according to claim 1, wherein generating the plurality of streams of accelerometer data samples comprises:

generating a non-filtered stream of accelerometer data samples, based on at least part of the input stream of accelerometer data samples; and generating a filtered stream of accelerometer data samples by digital low-pass filtering of samples of at least part of the input stream of accelerometer data samples.

3. The method of claim 1, wherein:

generating the plurality of streams of accelerometer data samples includes generating a non-filtered stream of accelerometer data samples;

the plurality of determined conditions of movement include a condition of rest and a condition of walking; and selecting a stream of accelerometer data samples of the plurality of streams of accelerometer data samples includes selecting the non-filtered stream of accelerometer data samples in response to identification of the condition of rest or the condition of walking.

4. The method of claim 1, wherein:

the plurality of determined conditions of movement include a condition of running, and selecting a stream of accelerometer data samples of the plurality of streams of accelerometer data samples includes selecting the filtered stream of samples in response to identification of the condition of running.

5. The method according to claim 1, wherein:

executing an automatic-learning algorithm comprises generating, for each block of the input stream of accelerometer data samples, a corresponding value of a classification signal, which is indicative of the condition of movement identified; and selecting a stream of accelerometer data samples of the plurality of streams of accelerometer data samples is executed based on the classification signal.

6. The method according to claim 1, wherein the executing an automatic-learning algorithm comprises, for each block of samples of the input stream of accelerometer data samples:

determining corresponding values of determined features of the block of samples of the input stream of accelerometer data samples; and executing a classification algorithm based on said corresponding values of determined features.

7. The method according to claim 6, wherein said determined features of the block of samples of the input stream of accelerometer data samples are chosen from among: variance, maximum or minimum of the block of samples of the input stream of accelerometer data samples, or of the Euclidean norms of the samples of said block of samples of the input stream of accelerometer data samples, or various combinations thereof.

8. The method according to claim 1, wherein the executing a wrist-tilt gesture detection algorithm comprises detecting whether the selected stream of accelerometer data samples exceeds a signal threshold for a threshold duration period.

9. The method according to claim 1, wherein the executing a wrist-tilt gesture detection algorithm comprises varying at least one parameter of said wrist-tilt detection algorithm based on the condition of movement identified.

10. The method according to claim 9, wherein said at least one parameter is a signal threshold or a duration threshold.

11. The method according to claim 1, comprising, for each condition of movement identified, selecting one of a first wrist-tilt gesture detection algorithm and at least a second wrist-tilt gesture detection algorithm, based on the condition of movement identified, and wherein said executing a wrist-tilt gesture detection algorithm comprises executing the selected wrist-tilt gesture detection algorithm.

12. The method of claim 1, wherein, the determined tilt angle of the axis of the plurality of axes of the wearable device is indicative of a tilt of an arm of a user to which the wearable device is constrained;

in response to the comparing indicating the determined tilt angle is less than or equal to the angle threshold, the selecting a type of data comprises selecting gyroscope data as the type of data to be used to detect wrist-tilt gestures; and in response to the comparing indicating the determined tilt angle is greater than the angle threshold, the selecting a type of data comprises selecting accelerometer data as the type of data to be used to detect wrist-tilt gestures.

13. A wearable device, comprising:

an input, which, in operation, receives an input stream of accelerometer data samples indicative of acceleration values along a plurality of axes of the wearable device; and circuitry, coupled to the input, wherein the circuitry, in operation:

based on the input stream of accelerometer data samples, determines a tilt angle of an axis of the plurality of axes of the wearable device with respect to a gravity direction;

compares the determined tilt angle to an angle threshold;

selects a type of data to be used to detect wrist-tilt gestures based on the comparing;

in response to selecting gyroscope data as the type of data to be used to detect wrist-tilt gestures, detects occurrence of a wrist-tilt gesture based on a set of samples of gyroscope data; and in response to selecting accelerometer data as the type of data to be used to detect wrist-tilt gestures:

executes an automatic-learning algorithm on blocks of samples of the input stream of accelerometer data samples to identify, for each block, corresponding conditions-of-user-movement from among a plurality of determined conditions-of-user-movement;

generates a plurality of streams of accelerometer data samples based on the input stream of accelerometer data samples, the plurality of streams of accelerometer data samples including a filtered stream of accelerometer data samples;

selects a stream of accelerometer data samples of the plurality of streams of accelerometer data samples based on an identified condition of user movement; and executes a wrist-tilt gesture detection algorithm using samples of the selected stream of the plurality of streams of samples of accelerometer data samples.

14. The wearable device according to claim 13, wherein the determined conditions-of-user-movement comprise at least one condition of rest or walking, and a condition of running; and the circuitry, in operation, generates the plurality of streams of accelerometer data samples by:

generating a non-filtered stream of accelerometer data samples, equal to at least part of the input stream of accelerometer data samples; and generating a filtered stream of accelerometer data samples by digital low-pass filtering of samples of at least part of the input stream of accelerometer data samples.

15. The wearable device according to claim 14, wherein the circuitry, in operation, selects the non-filtered stream of accelerometer data samples in response to identification of a condition of rest or a condition of walking.

16. The wearable device according to claim 14, wherein the circuitry, in operation, selects the filtered stream of accelerometer data samples in response to identification of a condition of running.

17. The wearable device according to claim 13, wherein the circuitry, in operation, generates, for each block of the input stream of accelerometer data samples, a corresponding value of a classification signal, which is indicative of the condition-of-user-movement identified, and selects the stream of samples of the plurality of streams of accelerometer data samples based on the classification signal.

18. The wearable device according to claim 13, wherein the circuitry, in operation:

determines corresponding values of determined features of a block of samples of the input stream of accelerometer data samples; and executes a classification algorithm based on said corresponding values of determined features.

19. The wearable device according to claim 13, wherein the circuitry, in operation, when accelerometer data is selected as the type of data to be used to detect wrist-tilt gestures, varies at least one parameter of the wrist-tilt gesture detection algorithm based on the condition-of-user-movement identified.

20. The wearable device according to claim 13, wherein the circuitry, in operation, when accelerometer data is selected as the type of data to be used to detect wrist-tilt gestures:

selects, for each condition of movement identified, one of a first wrist-tilt gesture detection algorithm and at least a second wrist-tilt gesture detection algorithm based on the condition-of-user-movement identified; and executes the selected wrist-tilt gesture detection algorithm.

21. The wearable device of claim 13, comprising:

an accelerometer coupled to the input, wherein the accelerometer, in operation, generates the stream of accelerometer data samples indicative of acceleration values along the plurality of axes of the wearable device.

22. The wearable device of claim 21, comprising:

a screen, wherein the circuitry, in operation, controls the screen based on a detected wrist-tilt gesture.

23. The wearable device of claim 21, comprising:

a gyroscope coupled to the circuitry, wherein the gyroscope, in operation, generates a gyroscope signal.

24. The wearable device of claim 13, wherein, the determined tilt angle of the axis of the plurality of axes of the wearable device is indicative of a tilt of an arm of a user to which the wearable device is constrained;

in response to the comparing indicating the determined tilt angle is less than or equal to the angle threshold, the selecting a type of data comprises selecting gyroscope data as the type of data to be used to detect wrist-tilt gestures; and in response to the comparing indicating the determined tilt angle is greater than the angle threshold, the selecting a type of data comprises selecting accelerometer data as the type of data to be used to detect wrist-tilt gestures.

25. A non-transitory computer-readable medium having contents which cause circuitry of a wearable device to perform a method, the method comprising:

receiving an input stream of accelerometer data samples from an accelerometer, the samples of the input stream of accelerometer data samples being indicative of acceleration values along a plurality of axes of a wearable device;

based on the input stream of accelerometer data samples, determining a tilt angle of an axis of the plurality of axes of the wearable device with respect to a gravity direction;

comparing the determined tilt angle to an angle threshold;

selecting a type of data to be used to detect wrist-tilt gestures based on the comparing;

in response to selecting gyroscope data as the type of data to be used to detect wrist-tilt gestures, detecting occurrence of a wrist-tilt gesture based on a set of samples of gyroscope data; and in response to selecting accelerometer data as the type of data to be used to detect wrist-tilt gestures:

executing an automatic-learning algorithm on blocks of samples of the input stream of accelerometer data samples to identify, for each block, corresponding conditions-of-user-movement from among a plurality of determined conditions-of-user-movement;

generating a plurality of streams of accelerometer data samples based on the input stream of accelerometer data samples, the plurality of streams of accelerometer data samples including a filtered stream of accelerometer data samples;

selecting a stream of accelerometer data samples of the plurality of streams of accelerometer data samples based on an identified condition of user movement; and executing a wrist-tilt gesture detection algorithm using samples of the selected stream of the plurality of streams of samples of accelerometer data samples.

26. The non-transitory computer-readable medium of claim 25, wherein the contents comprise instructions executed by the circuitry.

27. The non-transitory computer-readable medium of claim 25, wherein, the determined tilt angle of the axis of the plurality of axes of the wearable device is indicative of a tilt of an arm of a user to which the wearable device is constrained;

in response to the comparing indicating the determined tilt angle is less than or equal to the angle threshold, the selecting a type of data comprises selecting gyroscope data as the type of data to be used to detect wrist-tilt gestures; and in response to the comparing indicating the determined tilt angle is greater than the angle threshold, the selecting a type of data comprises selecting accelerometer data as the type of data to be used to detect wrist-tilt gestures.

* * * * *

UNITED STATES PATENT AND TRADEMARK OFFICE
CERTIFICATE OF CORRECTION

PATENT NO. : 12,204,694 B2
APPLICATION NO. : 17/862937
DATED : January 21, 2025
INVENTOR(S) : Federico Rizzardini et al.

It is certified that error appears in the above-identified patent and that said Letters Patent is hereby corrected as shown below:

In the Claims

Column 13, Claim 1, Line 22:
"a plurality of two or more streams" should read: --a plurality of streams--.

Signed and Sealed this
Eleventh Day of March, 2025

Coke Morgan Stewart
*Acting Director of the United States Patent and Trademark Office*